(12) United States Patent
Takezaki et al.

(10) Patent No.: US 11,268,937 B2
(45) Date of Patent: Mar. 8, 2022

(54) CAPACITIVE MICROMACHINED ULTRASONIC TRANSDUCER AND ULTRASONIC IMAGING APPARATUS USING THE SAME

(71) Applicant: HITACHI, LTD., Tokyo (JP)

(72) Inventors: Taiichi Takezaki, Tokyo (JP); Shuntaro Machida, Tokyo (JP); Daisuke Ryuzaki, Tokyo (JP); Yasuhiro Yoshimura, Tokyo (JP); Tatsuya Nagata, Tokyo (JP); Naoaki Yamashita, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 553 days.

(21) Appl. No.: 16/315,676

(22) PCT Filed: Jul. 6, 2017

(86) PCT No.: PCT/JP2017/024816
§ 371 (c)(1),
(2) Date: Jan. 7, 2019

(87) PCT Pub. No.: WO2018/037730
PCT Pub. Date: Mar. 1, 2018

(65) Prior Publication Data
US 2019/0170699 A1 Jun. 6, 2019

(30) Foreign Application Priority Data
Aug. 24, 2016 (JP) .............................. JP2016-163794

(51) Int. Cl.
*H04R 19/00* (2006.01)
*G01N 29/24* (2006.01)
(Continued)

(52) U.S. Cl.
CPC ....... *G01N 29/2406* (2013.01); *A61B 8/4477* (2013.01); *A61B 8/4483* (2013.01); *B06B 1/0292* (2013.01); *G01N 29/265* (2013.01)

(58) Field of Classification Search
None
See application file for complete search history.

(56) References Cited

U.S. PATENT DOCUMENTS 9,846,145 B2  12/2017 Koshimura et al.
10,603,689 B2   3/2020 Machida et al.
(Continued)

FOREIGN PATENT DOCUMENTS

CN    1428206 A  *  7/2003  .......... G01N 29/245
CN  101238754 A  *  8/2008
(Continued)

OTHER PUBLICATIONS

International Search Report of PCT/JP2017/024816 dated Aug. 1, 2017.
(Continued)

*Primary Examiner* — Isam A Alsomiri
*Assistant Examiner* — Jonathan D Armstrong
(74) *Attorney, Agent, or Firm* — Mattingly & Malur, PC

(57) ABSTRACT

A capacitive micromachined ultrasonic transducer 111A includes: a silicon substrate 101; an insulating film 102 formed over the silicon substrate 101; a lower electrode 103; insulating films 104 and 106; a cavity 105 constituted by a void formed in a portion of the insulating film 106; an upper electrode 107; insulating films 108 and 114; and a protective film 109. In addition, the insulating film 106, upper electrode 107, insulating film 108 and insulating film 114 above the cavity 105 configure a vibration film 110, and the protective film 109 above the vibration film 110 is divided into a
(Continued)

plurality of isolated patterns regularly arranged with a gap 115 having a constant spacing formed therebetween.

6 Claims, 10 Drawing Sheets

(51) Int. Cl.
  *G01N 29/265* (2006.01)
  *A61B 8/00* (2006.01)
  *B06B 1/02* (2006.01)

(56) References Cited

U.S. PATENT DOCUMENTS

| | | | | |
|---|---|---|---|---|
| 2007/0193354 A1* | 8/2007 | Felix | ............... | B06B 1/0292 |
| | | | | 73/514.32 |
| 2009/0082673 A1* | 3/2009 | Lu | ............... | B06B 1/0622 |
| | | | | 600/459 |
| 2010/0123366 A1 | 5/2010 | Chang | | |
| 2013/0071964 A1* | 3/2013 | Kato | ............... | H04R 31/00 |
| | | | | 438/50 |
| 2014/0219062 A1* | 8/2014 | Rothberg | ............... | G10K 9/12 |
| | | | | 367/135 |
| 2015/0323657 A1 | 11/2015 | Machida et al. | | |
| 2016/0030004 A1* | 2/2016 | Nakazawa | ............... | A61B 8/4488 |
| | | | | 600/447 |
| 2017/0291192 A1* | 10/2017 | Machida | ............... | B06B 1/0607 |
| 2018/0078970 A1* | 3/2018 | Ono | ............... | H01L 41/0533 |
| 2019/0160491 A1* | 5/2019 | Biateau | ............... | B06B 1/0292 |

FOREIGN PATENT DOCUMENTS

| | | | | |
|---|---|---|---|---|
| CN | 101238754 A | | 8/2008 | |
| CN | 104114097 A | * | 10/2014 | ........... B06B 1/0292 |
| CN | 104114097 A | | 10/2014 | |
| DE | 102008022215 A1 | * | 11/2009 | ............. G01N 9/002 |
| JP | 2010-154734 A | | 7/2010 | |
| JP | 2014-120874 A | | 6/2014 | |
| JP | 2016-072661 A | | 5/2016 | |
| WO | WO-2005120130 A1 | * | 12/2005 | ........... B06B 1/0292 |
| WO | WO-2013059358 A2 | * | 4/2013 | ........... A61B 8/5207 |
| WO | 2016/047186 A1 | | 3/2016 | |
| WO | WO-2016047186 A1 | * | 3/2016 | ........... B06B 1/0607 |
| WO | WO-2018019778 A1 | * | 2/2018 | ........... B06B 1/0292 |
| WO | WO-2018037730 A1 | * | 3/2018 | ........... A61B 8/4477 |

OTHER PUBLICATIONS

Chinese Office Action received in corresponding Chinese Application No. 201780027702.0 dated Mar. 29, 2021.
Chinese Office Action dated Oct. 12, 2020, issued in corresponding Chinese Patent Application No. 201780027702.
Chinese Office Action received in corresponding Chinese Application No. 201780027702.0 dated Jul. 30, 2021.

\* cited by examiner (a)

(b)

(c)

(d)

(e)

CAPACITIVE MICROMACHINED ULTRASONIC TRANSDUCER AND ULTRASONIC IMAGING APPARATUS USING THE SAME

TECHNICAL FIELD

The present invention relates to a capacitive micromachined ultrasonic transducer and an ultrasonic imaging apparatus using the same.

BACKGROUND ART

Conventionally, piezoelectric ceramics typified by PZT (lead zirconate titanate) or the like have been utilized as an electroacoustic conversion element in a probe of an ultrasonic imaging apparatus. However, capacitive micromachined ultrasonic transducers (CMUTs) having wider band characteristics than the piezoelectric ceramics have been attracting more attention and have been subject to research and development for the past few years (Patent Document 1).

The capacitive micromachined ultrasonic transducer has a a cavity formed above a semiconductor substrate and covered by an insulating film, a lower electrode is arranged on a lower side of the cavity, and a vibration film (diaphragm) that includes an upper electrode is arranged on an upper side of the cavity.

Here, operating principles of the capacitive micromachined ultrasonic transducer will be described. By applying a voltage between the lower electrode and the upper electrode and generating a potential difference, an electrostatic force is generated in the vibration film above the cavity. When transmitting an ultrasonic wave, the electrostatic force applied to the vibration film is temporally varied by applying an AC voltage superimposed on a DC bias voltage, thereby vibrating the vibration film. On the other hand, when receiving an ultrasonic wave, displacement of the vibration film is detected as a capacitance change between the upper and lower electrodes in a state where a constant DC bias voltage is being applied.

The capacitive micromachined ultrasonic transducer utilizes a silicon wafer or the like as the substrate and is manufactured by a semiconductor fabricating process. In the final step of the manufacturing process, a protective film made of an organic film or the like is formed over an outermost surface of the capacitive micromachined ultrasonic transducer, and thereafter, thinning of the substrate by backgrinding and singulation by dicing are performed.

In addition, the singulated capacitive micromachined ultrasonic transducer is bonded to a backing material in order to absorb unnecessary ultrasonic waves radiated on a back side of the substrate. When the transducer is bonded to the backing material, a surface of the capacitive micromachined ultrasonic transducer is pressed into contact. After an electrical connection terminal is attached, an acoustic lens that converges the ultrasonic waves is then attached to a front side of the capacitive micromachined ultrasonic transducer. Then, after electric components are attached as necessary, a probe cable and a case are attached to complete the ultrasonic probe.

RELATED ART DOCUMENTS

Patent Documents

Patent Document 1: Japanese Unexamined Patent Application
Publication No. 2010-154734

SUMMARY OF THE INVENTION

Problems to be Solved by the Invention

The protective film formed over the surface of the capacitive micromachined ultrasonic transducer adds excessive mass to the vibration film and occasionally causes a decrease in sensitivity of the vibration film.

As a countermeasure, it is considered that limiting the formation of the protective film to only the vicinity of the electrodes and wirings of the capacitive micromachined ultrasonic transducer as in Patent Document 1 can suppress a decrease in sensitivity while ensuring insulation properties.

However, if foreign matter adheres to a region where the protective film is not formed and the surface of the singulated capacitive micromachined ultrasonic transducer is being pressed into contact to be mounted on the backing material, the vibration film is directly pressed by the foreign matter since a cushioning effect by the protective film cannot be obtained. This may lead to destruction of the protective film and cause a decrease in manufacturing yield of the ultrasonic probe. In particular, the ultrasonic transducer operating in a low frequency band has a vibration film that is thin, raising concerns regarding an increase in the probability of destruction.

Therefore, there is a growing demand to devise the capacitive micromachined ultrasonic transducer such that a decrease in the manufacturing yield can be suppressed without causing a decrease in sensitivity of the vibration film.

The above-described objects, other objects and novel features of the present invention will be apparent from the description in the present specification and the attached drawings.

Means for Solving the Problems

The following briefly describes an overview of a representative embodiment disclosed in the present application.

In the capacitive micromachined ultrasonic transducer according to the representative embodiment, a protective film above a vibration film is divided into a plurality of patterns arranged with a gap having a predetermined spacing formed therebetween.

Effects of the Invention

According to the representative embodiment of the capacitive micromachined ultrasonic transducer, a decrease in the manufacturing yield can be suppressed without causing a decrease in sensitivity of the vibration film.

DETAILED DESCRIPTION OF PREFERRED EMBODIMENTS

Figure 1:
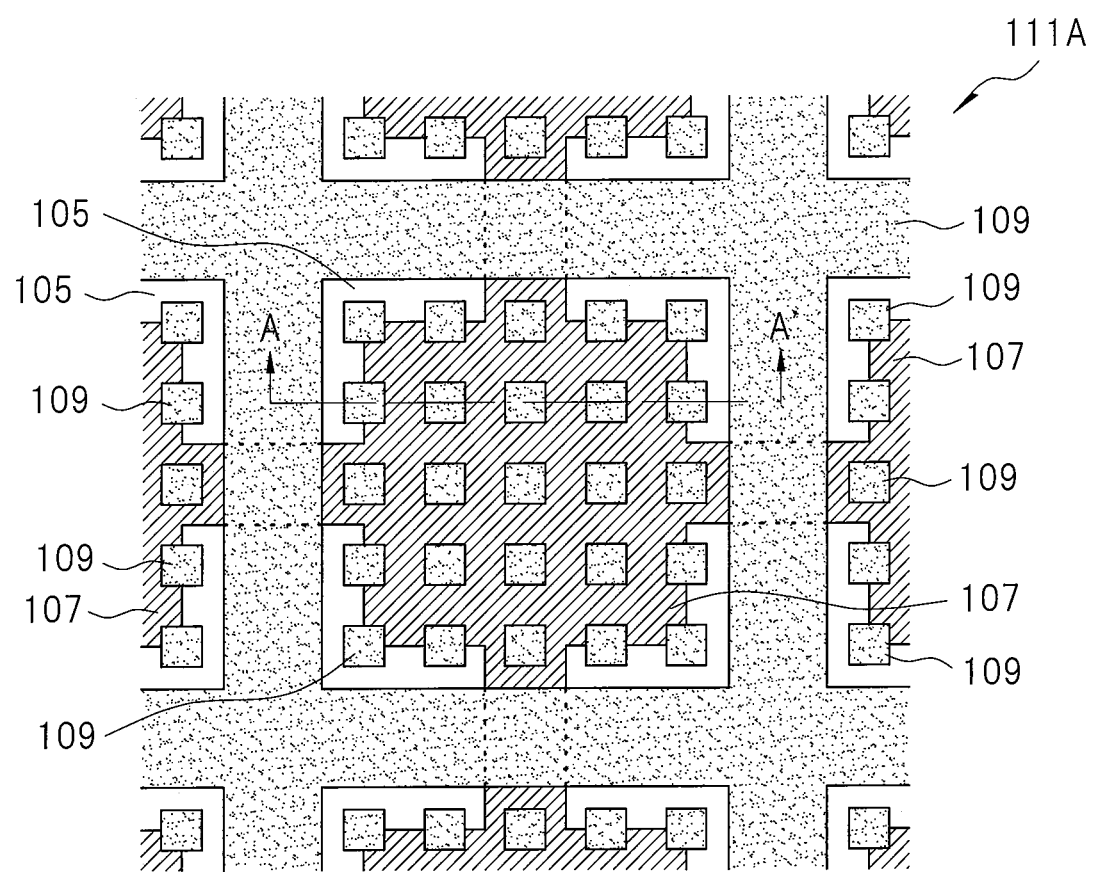
FIG. 1 is a plan view showing a main part of a capacitive micromachined ultrasonic transducer according to a first embodiment.

Hereinafter, embodiments according to the present invention will be described in detail with reference to the drawings. Note that, in all of the drawings used to describe the embodiments, members having the same functions are denoted by the same reference signs, and redundant descriptions thereof are omitted as appropriate. In addition, in the embodiments, descriptions of the same or similar components will not be repeated in principle unless otherwise particularly necessary. Further, in the drawings used to describe the embodiments, hatched lines may occasionally be added even in a plan view or may occasionally be omitted even in a cross-sectional view in order to make the configuration easier to understand.

First Embodiment

Figure 2:
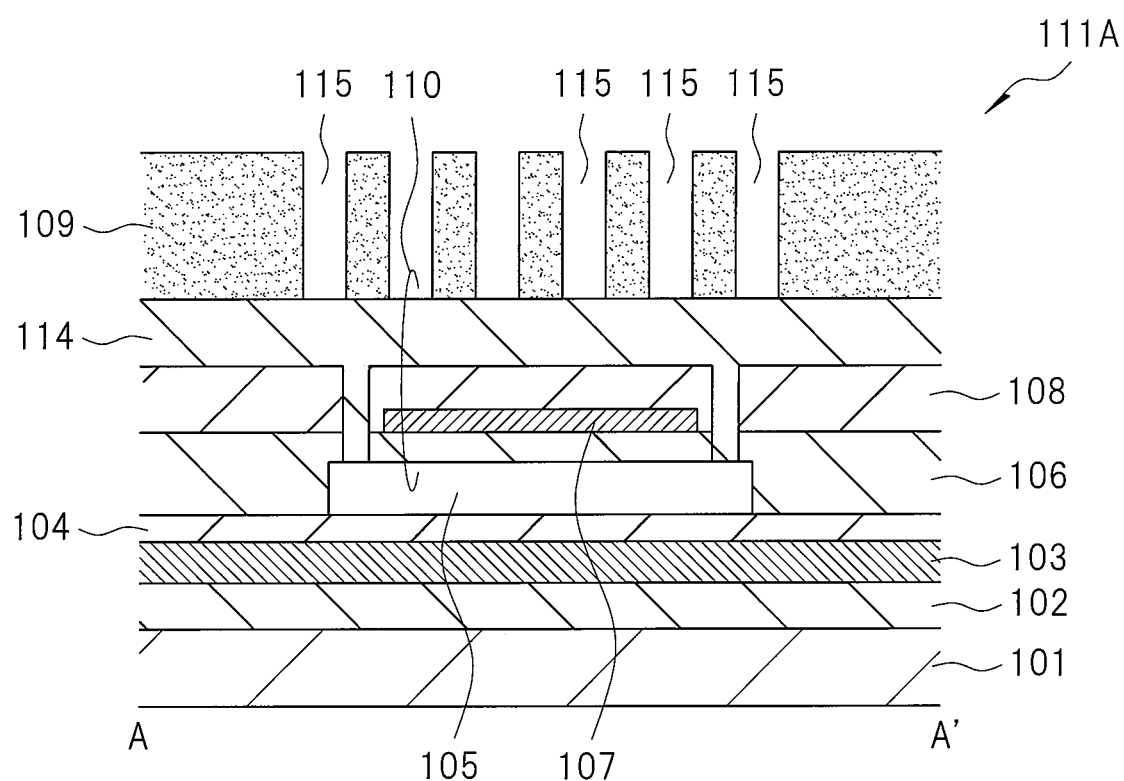
FIG. 2 is a cross-sectional view taken along a line A-A' of FIG. 1.

FIG. 1 is a plan view showing a main part of a capacitive micromachined ultrasonic transducer according to a first embodiment, and FIG. 2 is a cross-sectional view taken along a line A-A' of FIG. 1.

The capacitive micromachined ultrasonic transducer 111A of the first embodiment comprises: a silicon substrate 101; an insulating film 102 formed over the silicon substrate 101; a lower electrode 103; insulating films 104 and 106; a cavity 105 constituted by a void formed in a portion of the insulating film 106; an upper electrode 107; insulating films 108 and 114; and a protective film 109. In addition, the insulating film 106, upper electrode 107, insulating film 108 and insulating film 114 above the cavity 105 configure a vibration film 110.

Examples of materials of the insulating films 102, 104, 106, 108 and 114 include $Si_xO_Y$ (silicon oxide), $Si_xN_Y$ (silicon nitride), $Si_xO_YN_Z$ (silicon oxynitride), $Hf_xO_Y$ (hafnium oxide), Y-doped $Hf_xO_Y$ (yttrium-doped hafnium oxide), Si-doped $Hf_xO_Y$ (silicon-doped hafnium oxide), $La_x$-$Ta_YO_Z$ (lanthanum oxide+tantalum oxide) and the like. In addition, it is preferable that the film thickness of each of the films is within a range of 10 nm to 5000 nm.

It is preferable that a height of the cavity 105 is within a range of 10 nm to 5000 nm. FIG. 1 shows an example in which a planar shape of the cavity 105 is a quadrangle. However, the planar shape of the cavity 105 is not limited to be a quadrangle, and may be any shape such as a circle, a polygon or the like. In addition, in a case where the planar shape of the cavity 105 is a quadrangle, it is preferable that a planar size of the cavity 105 is set such that each side has a length within a range of approximately 100 nm to 1000000 nm, depending on a frequency band of the vibration film 110.

The electromechanical coupling coefficient which is one of the factors used for determining sensitivity of the capacitive micromachined ultrasonic transducer 111A increases as a distance between the upper and lower electrodes decreases. However, if this distance is too short, the insulating films interposed between the upper and lower electrodes may come into contact and cause dielectric breakdown, or alternatively, a moving range of the vibration film 110 may become narrowed and prevent a sufficient transmitted acoustic pressure from being obtained. Therefore, it is more preferable that the film thickness of each of the insulating films (insulating film 104 and insulating film 106) interposed between the upper and lower electrodes is within a range of 10 nm to 1000 nm, and it is more preferable that the height of the cavity 105 is within a range of 10 nm to 1000 nm.

Examples of materials of the lower electrode 103 and the upper electrode 107 can be selected from metals, highly-concentrated impurity-doped semiconductors and the like, including W, Ti, TiN, Al, Cr, Pt, Au, Si, poly-Si, amorphous-Si and the like. In addition, it is preferable that the film thickness of each of the films is within a range of 10 nm to 1000 nm.

When a surface of the capacitive micromachined ultrasonic transducer 111A is being pressed into contact to bond the capacitive micromachined ultrasonic transducer 111A to a backing material, the protective film 109 provides a cushioning effect against the foreign matter adhered to the surface of the capacitive micromachined ultrasonic transducer 111A and prevents the vibration film 110 from being directly pressed by the foreign matter which leads to destruction of the vibration film 110.

In the capacitive micromachined ultrasonic transducer 111A of the first embodiment, the protective film 109 above the vibration film 110 is divided into a plurality of isolated patterns regularly arranged with a gap 115 having a constant spacing formed therebetween.

Examples of the material of the protective film 109 include polyimide resin, polybenzoxazole resin, polydimethylsiloxane resin, parylene resin, polymethyl methacrylate resin and the like. In addition, it is preferable that a film thickness of the protective film 109 is within a range of 100 nm to 10000 nm, depending on the size of the foreign matter adhered to the surface of the capacitive micromachined ultrasonic transducer 111A. It is preferable that a planar size of each of the isolated patterns in the protective film 109 is within a range of 10 nm to 1000000 nm, depending on the size of the cavity 105.

In the first embodiment, the upper electrode 107 is covered by the insulating film 108 and insulating film 114, and in a case where the capacitive micromachined ultrasonic transducer 111A is applied to an ultrasonic imaging apparatus, these become an element that ensures insulation properties between the apparatus and a subject. Further, using a material having insulation properties for the protective film 109 allows the protective film 109 to become another element that ensures insulation properties between the apparatus and the subject.

In the example shown in FIGS. 1 and 2, a single lower electrode 103 and a single upper electrode 107 is formed per cavity 105. However, the lower electrode 103 and the upper electrode 107 may each be divided into a plurality of sections. In this case, a shape of the vibration film 110 can be controlled by transmitting different electric signals to each of the divided electrodes. Alternatively, the divided electrodes may be connected in parallel, so that the same electric signals are transmitted to each of the electrodes.

Figure 3:
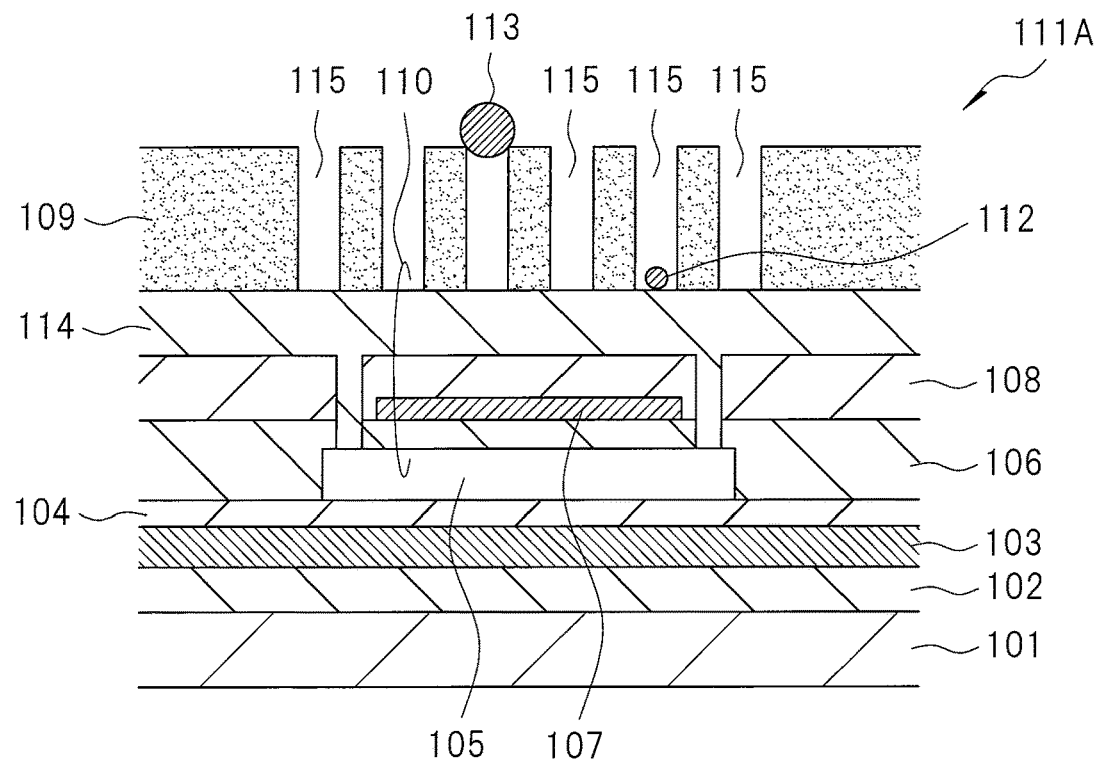
FIG. 3 is a cross-sectional view describing an effect of the capacitive micromachined ultrasonic transducer according to the first embodiment.

Next, effects of the first embodiment will be described. FIG. 3 is a cross-sectional view showing a state where two types of foreign matter having different sizes have adhered to a portion (portion corresponding to the line A-A' of FIG. 1) of the surface of the capacitive micromachined ultrasonic transducer 111A.

The first foreign matter 112 has a size that is smaller than the spacing of the gap 115 in the protective film 109 and is present on a surface of the vibration film 110. Here, the foreign matter 112 is considered to be the only foreign matter on the surface of the capacitive micromachined ultrasonic transducer 111A. When the capacitive micromachined ultrasonic transducer 111A is pressed into contact in this state with using a pressing piece and the capacitive micromachined ultrasonic transducer 111A is bonded to the backing material, the surface of the protective film 109 becomes the surface in contact with the pressing piece, whereby a cushioning effect is provided by the protective film 109. In this case, possibility of destruction of the vibration film 110 is low since the vibration film 110 is not directly pressed by the foreign matter 112.

On the other hand, the second foreign matter 113 has a size that is larger than the spacing of the gap 115 in the protective film 109 and is present on the surface of the protective film 109. Here, the foreign matter 113 is considered to be the only foreign matter on the surface of the capacitive micromachined ultrasonic transducer 111A. When the capacitive micromachined ultrasonic transducer 111A is pressed into contact in this state with using the pressing piece and the capacitive micromachined ultrasonic transducer 111A is bonded to the backing material, the foreign matter 113 becomes the surface in contact with the pressing piece, whereby a cushioning effect is provided by the protective film 109. In this case also, possibility of destruction of the vibration film 110 is low since the vibration film 110 is not directly pressed by the foreign matter 113.

In order to obtain a sufficient cushioning effect by the protective film 109, it is necessary to optimize the thickness of the protective film 109 and the spacing of the gap 115 with respect to the size of the foreign matter. Namely, it is preferable that the thickness of the protective film 109 is greater than the size of the foreign matter such that the foreign matter in contact with the vibration film 110 is not directly pressed. In addition, it is preferable that the spacing of the gap 115 in the protective film 109 is smaller than the size of the foreign matter such that the foreign matter does not directly come in contact with the vibration film 110. By statistically analyzing the size of the foreign matter that adheres to the capacitive micromachined ultrasonic transducer 111A during a step of mounting the capacitive micromachined ultrasonic transducer 111A on the backing material and determining the thickness of the protective film 109 and the spacing of the gap 115 based on the above-described relation, probability of destruction of the vibration film 110 during the mounting step can be reduced.

In addition, when bonding an acoustic lens to the capacitive micromachined ultrasonic transducer 111A bonded to the backing material, either the surface of the protective film 109 or the foreign matter becomes the surface in contact with the acoustic lens depending on the size of the foreign matter, whereby a cushioning effect is provided by the protective film 109. In this case also, possibility of destruction of the vibration film 110 is low since the vibration film 110 is not directly pressed by the foreign matter.

The first embodiment has described a case where the thickness and planar size of each of the isolated patterns in the protective film 109 are constant across the entire surface of the vibration film 110 and where the spacing of each of the gaps 115 in the protective film 109 is also constant. In this case, a uniform cushioning effect by the protective film can be obtained across the entire surface of the vibration film 110, whereby probability of destruction of the vibration film 110 caused by the foreign matter adhered during the mounting step is reduced. In addition, it is obvious that the same effects as describe above can be obtained even if the thickness and planar size of the protective film 109 are not constant across the entire surface of the vibration film 110 unlike the case described above.

Figure 4:
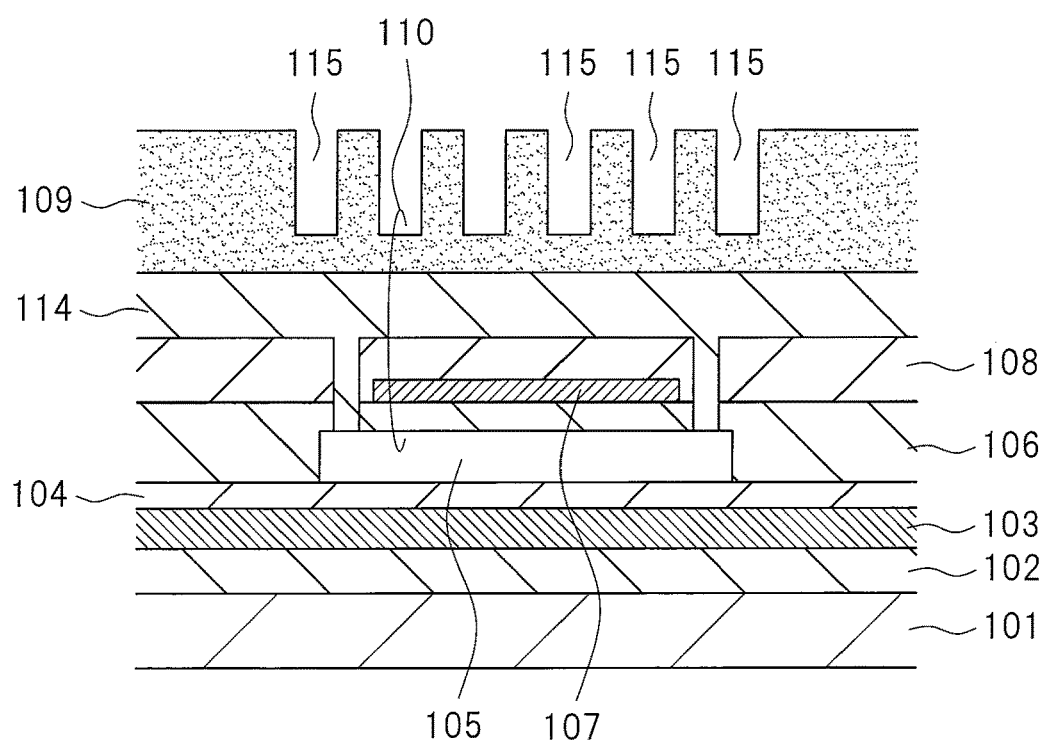
FIG. 4 is a cross-sectional view showing a modification of the capacitive micromachined ultrasonic transducer according to the first embodiment.

FIG. 4 shows an example in which a bottom portion of the gap 115 in the protective film 109 does not reach the surface of the vibration film 110.

In this case also, the same effects as those described above in the first embodiment can be obtained. In addition, a cushioning effect that acts against the foreign matter having entered the gap 115 in the protective film 109 is provided by the protective film 109 present at the bottom portion of the gap 115.

However, since the protective film 109 is not completely divided into a plurality of isolated patterns in this case, influence of viscoelasticity of the protective film becomes large when a voltage is applied between the upper and lower electrodes and the vibration film 110 is deformed, whereby an amount of deformation becomes unstable and creep deformation in which the amount of deformation varies over a period of time occurs. As a result, a distance between the upper and lower electrodes becomes short during operation and may cause dielectric breakdown to occur. Therefore, from the viewpoint of preventing dielectric breakdown, it is preferable that the protective film 109 is constituted by a plurality of isolated patterns completely separated from each other as in the example shown in FIGS. 1 and 2.

As described above, by providing the gap 115 in the protective film 109 above the vibration film 110, possibility of the foreign matter directly pressing the vibration film 110 is reduced, and thus, probability of destruction of the vibration film 110 during the mounting step is reduced while suppressing a decrease in a mounting yield of the capacitive micromachined ultrasonic transducer 111A. In particular, the thin vibration film 110 of the capacitive micromachined ultrasonic transducer 111A operating in a low frequency band is expected to provide an effect in which the mounting yield is significantly improved.

Figure 5:
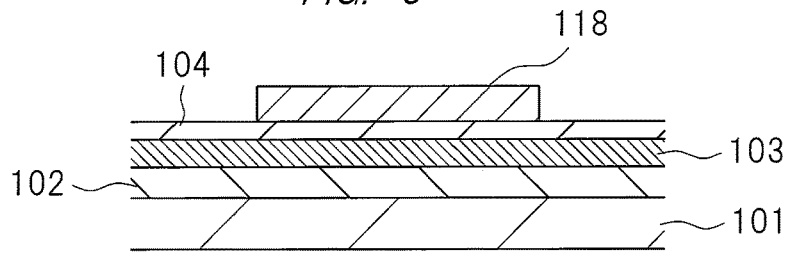
FIGS. 5(a) to 5(e) are cross-sectional views each showing a manufacturing method of the capacitive micromachined ultrasonic transducer according to the first embodiment.
Figure 5:
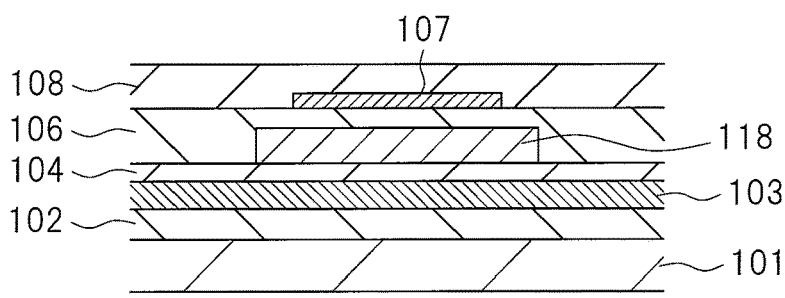
Figure 5:
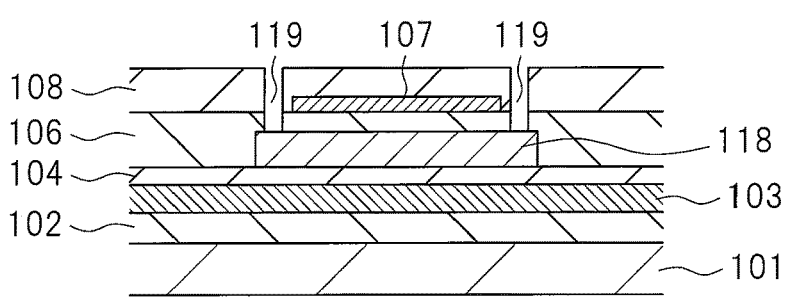
Figure 5:
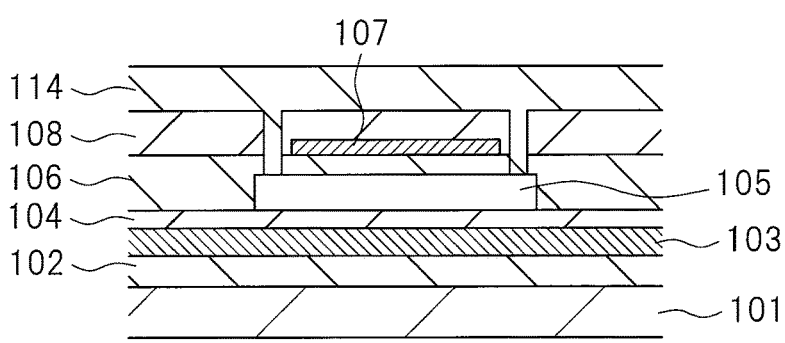
Figure 5:
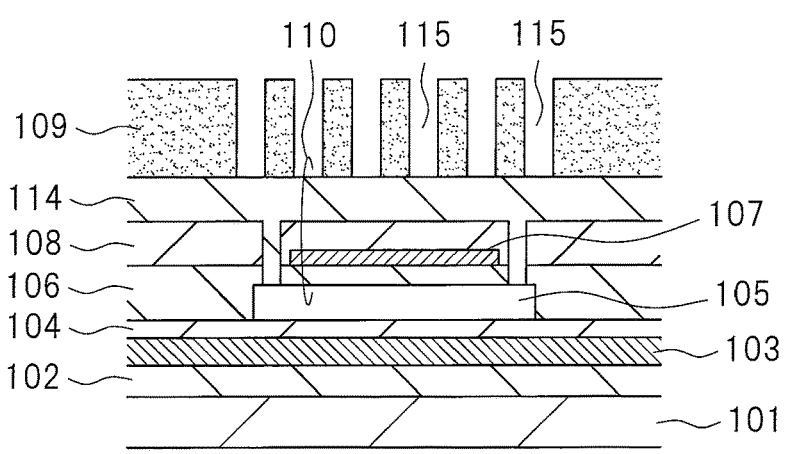

Next, a manufacturing method of the capacitive micromachined ultrasonic transducer 111A of the first embodiment will be described with reference to FIG. 5. FIG. 5 includes cross-sectional views corresponding to a cross section taken along the line A-A' of FIG. 1.

First, as shown in FIG. 5(a), the insulating film 102, lower electrode 103 and insulating film 104 are sequentially deposited over the silicon substrate 101, a metal film 118 is then deposited over the insulating film 104, and thereafter, the metal film 118 is patterned by a lithography method so as to form a shape of the cavity 105. Note that a semiconductor film, an insulating film or the like may be patterned instead of the metal film 118 so as to form the shape of the cavity 105.

Next, as shown in FIG. 5(b), the insulating film 106 is deposited so as to cover the insulating film 104 and the metal film 118, a metal film (or a highly-concentrated impurity-doped semiconductor film or the like) is then deposited over the insulating film 106 and is patterned by the lithography method to form the upper electrode 107, and thereafter, the insulating film 108 is deposited so as to cover the insulating film 106 and the upper electrode 107.

Next, as shown in FIG. 5(c), the insulating films 108 and 106 above the metal film 118 are etched to form a cavity-forming hole 119 that reaches a surface of the metal film 118.

Next, as shown in FIG. 5(d), an etching solution is injected into the cavity-forming hole 119, the metal film 118 is then melted to form the cavity 105, and thereafter, the insulating film 114 is deposited over the insulating film 108 to seal the cavity-forming hole 119.

Next, as shown in FIG. 5(e), the protective film 109 is formed over the insulating film 114. The protective film 109 is formed by depositing a protective film material over the insulating film 114 by, for example, a spin-coating method or a vapor-phase growth method such as sputtering, vapor deposition, CVD and the like, and then, if the protective film material is photosensitive, the protective film material is patterned by the lithography method to form the protective film 109 having the gaps 115. In addition, if the protective film material is non-photosensitive, the insulating film, the metal film, the organic film and the like deposited over the protective film material are patterned by the lithography method, and then, the protective film material is etched with using the pattern as a mask to form the protective film 109 having the gaps 115.

Second Embodiment

Figure 6:
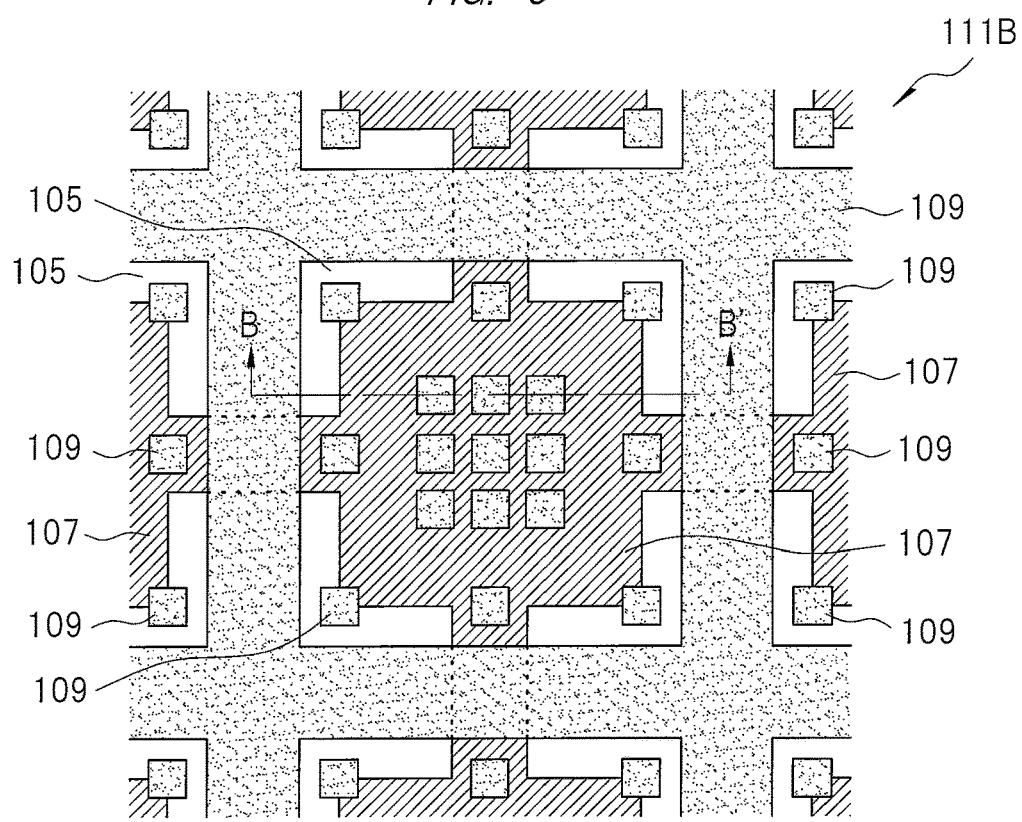
FIG. 6 is a plan view showing a main part of the capacitive micromachined ultrasonic transducer according to a second embodiment.
Figure 7:
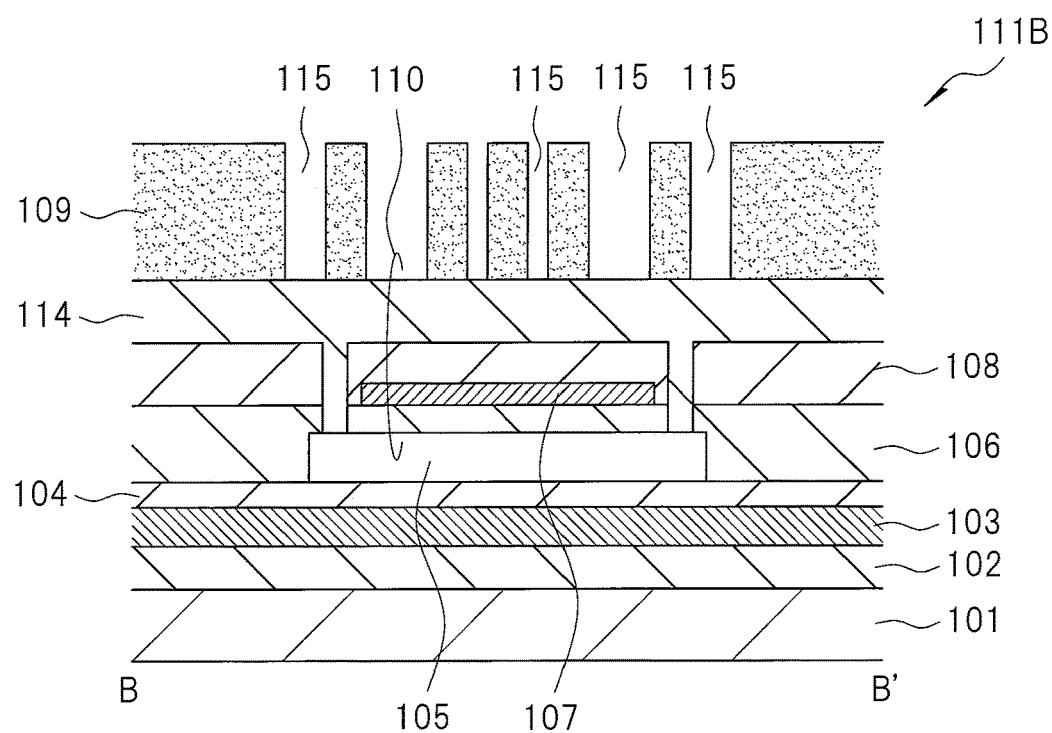
FIG. 7 is a cross-sectional view taken along a line B-B' of FIG. 6.

FIG. 6 is a plan view showing a main part of the capacitive micromachined ultrasonic transducer according to a second embodiment, and FIG. 7 is a cross-sectional view taken along a line B-B' of FIG. 6.

The capacitive micromachined ultrasonic transducer 111B of the second embodiment differs from the capacitive micromachined ultrasonic transducer 111A of the first embodiment in methods of arranging the isolated patterns in the protective film 109.

Namely, in the first embodiment, the thickness and planar size of each of the isolated patterns in the protective film 109 are constant across the entire upper surface of the vibration film 110, and the spacing of each of the gaps 115 in the protective film 109 is also constant. However, in the example shown in FIGS. 6 and 7, although the thickness and planar size of each of the isolated patterns are constant across the entire upper surface of the vibration film 110, the spacing of each of the gaps 115 is not constant. In particular, the number of protective films 109 above a peripheral portion of the vibration film 110 is relatively small, whereas the number of protective films 109 above a center portion of the vibration film 110 is relatively large. In other words, density of the isolated patterns above the peripheral portion of the vibration film 110 is low, whereas density of the isolated patterns above a center portion of the cavity 105 is high.

Next, effects of the second embodiment shown in FIGS. 6 and 7 will be described. In the capacitive micromachined ultrasonic transducer 111B of the second embodiment, stiffness of the vibration film 110 is relatively high at its peripheral portion and is relatively low at its center portion. For this reason, when the foreign matter in contact with the vibration film 110 is pressed into contact, destruction is unlikely to occur at the peripheral portion of the vibration film 110 since the amount of deformation is small, whereas destruction is more likely to occur at the center portion of the vibration film 110 since the amount of deformation is large.

Thus, even if a pattern density of the protective film 109 above the peripheral portion of the vibration film 110 is relatively low, it is considered that there is little influence on destruction of the vibration film 110.

On the other hand, from the viewpoint of suppressing a decrease in sensitivity of the vibration film 110, it is preferable that a mass of the protective film 109 is reduced. Namely, the pattern density of the protective film 109 above the peripheral portion of the vibration film 110 is configured to be relatively low, so that a decrease in both yield and sensitivity can be suppressed.

In addition, from the viewpoint of creep deformation, it is preferable that the pattern density of the protective film 109 above the peripheral portion of the vibration film 110 is relatively low, and this will be described below.

When a voltage is applied between the upper and lower electrodes and the vibration film 110 is deformed so as to be recessed, a greater stress is applied to the protective film 109 above the peripheral portion of the vibration film 110 than to the protective film 109 above the center portion of the vibration film 110. For this reason, the protective film 109 above the peripheral portion of the vibration film 110 has a greater influence on creep deformation than the protective film 109 above the center portion of the vibration film 110.

Therefore, the pattern density of the protective film 109 above the peripheral portion of the vibration film 110 is configured to be relatively low as in the second embodiment, so that influence on creep deformation can be reduced. In this manner, from the viewpoint of creep deformation, it is preferable that the pattern density of the protective film 109 above the peripheral portion of the vibration film 110 is relatively low.

Figure 8:
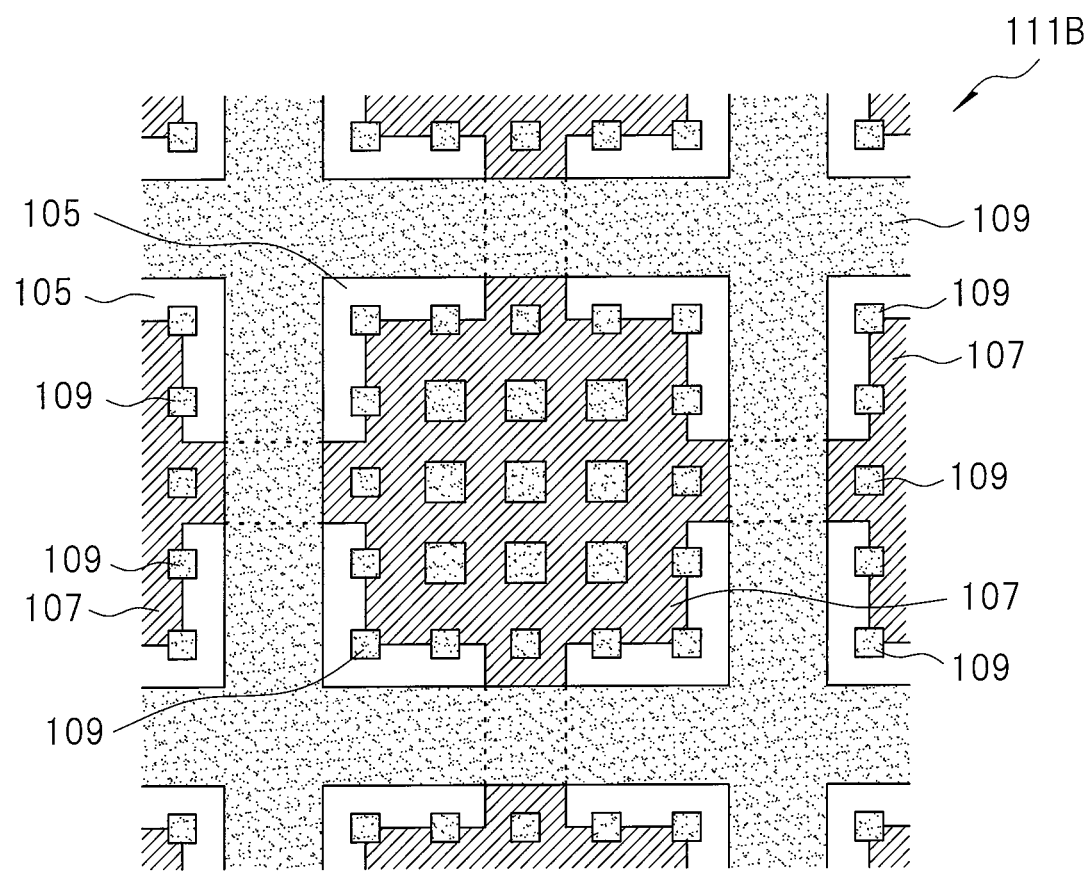
FIG. 8 is a plan view showing a modification of the capacitive micromachined ultrasonic transducer according to the second embodiment.

The method of providing the protective film 109 such that the pattern densities differ between the portion above the peripheral portion of the vibration film 110 and the portion above the center portion of the vibration film 110 is not limited to the example shown in FIGS. 6 and 7, and the planar size of each of the isolated patterns in the protective film 109 may differ between the portion above the peripheral portion of the vibration film 110 and the portion above the center portion of the vibration film 110 as shown in, for example, FIG. 8. Namely, the planar size of each of the isolated patterns in the protective film 109 above the peripheral portion of the vibration film 110 may be relatively small, whereas the planar size of each of the isolated patterns in the protective film 109 above the center portion of the vibration film 110 may be relatively large.

Figure 9:
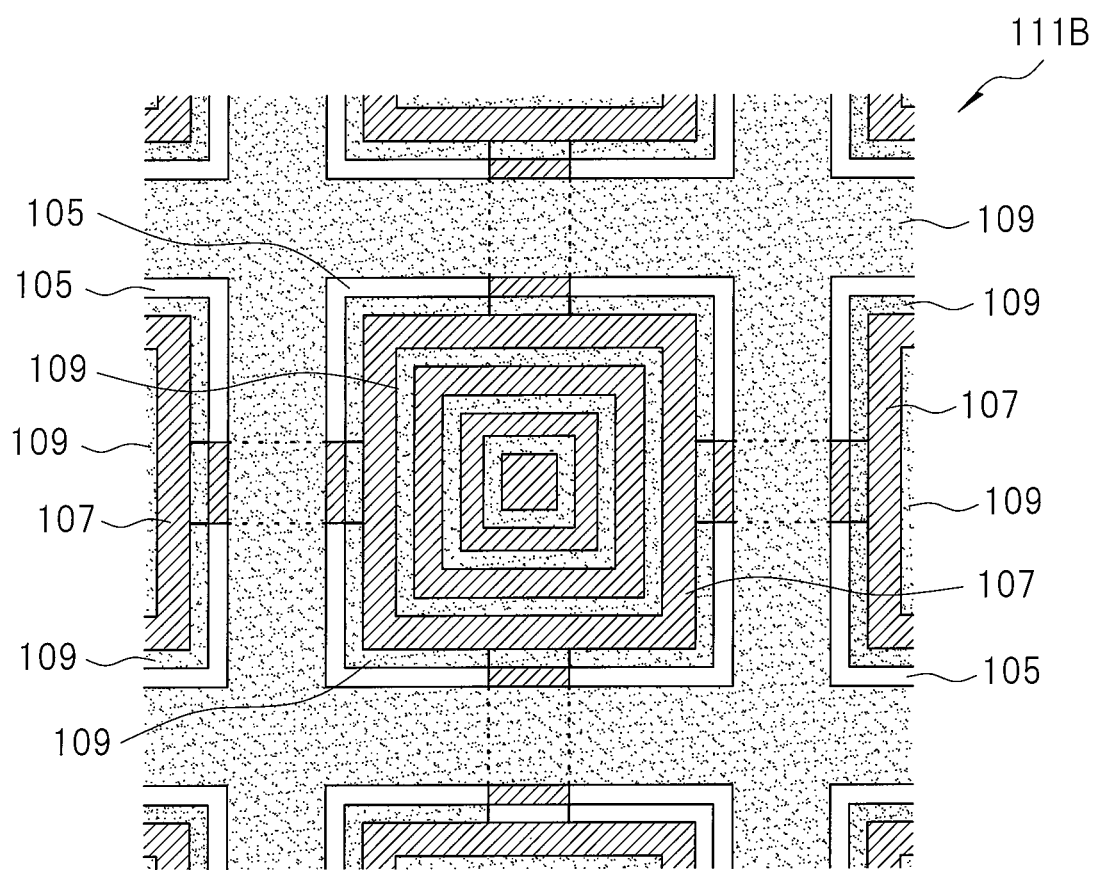
FIG. 9 is a plan view showing a modification of the capacitive micromachined ultrasonic transducer according to the second embodiment.

In the above-described example, the pattern densities of the protective film 109 differ between the portion above the peripheral portion of the vibration film 110 and the portion above the center portion of the vibration film 110. However, the pattern density of the protective film 109 may be configured so as to gradually increase from the portion above the peripheral portion of the vibration film 110 toward the portion above the center portion of the vibration film 110 as shown in, for example, FIG. 9.

To summarize, the pattern density of the protective film 109 is configured to be low at the portion above the peripheral portion of the vibration film 110 and high at the portion above the center portion of the vibration film 110, so that a decrease in sensitivity of the vibration film 110 and an occurrence of creep deformation can be suppressed without causing a decrease in the manufacturing yield of the capacitive micromachined ultrasonic transducer 111B.

Third Embodiment

Figure 10:
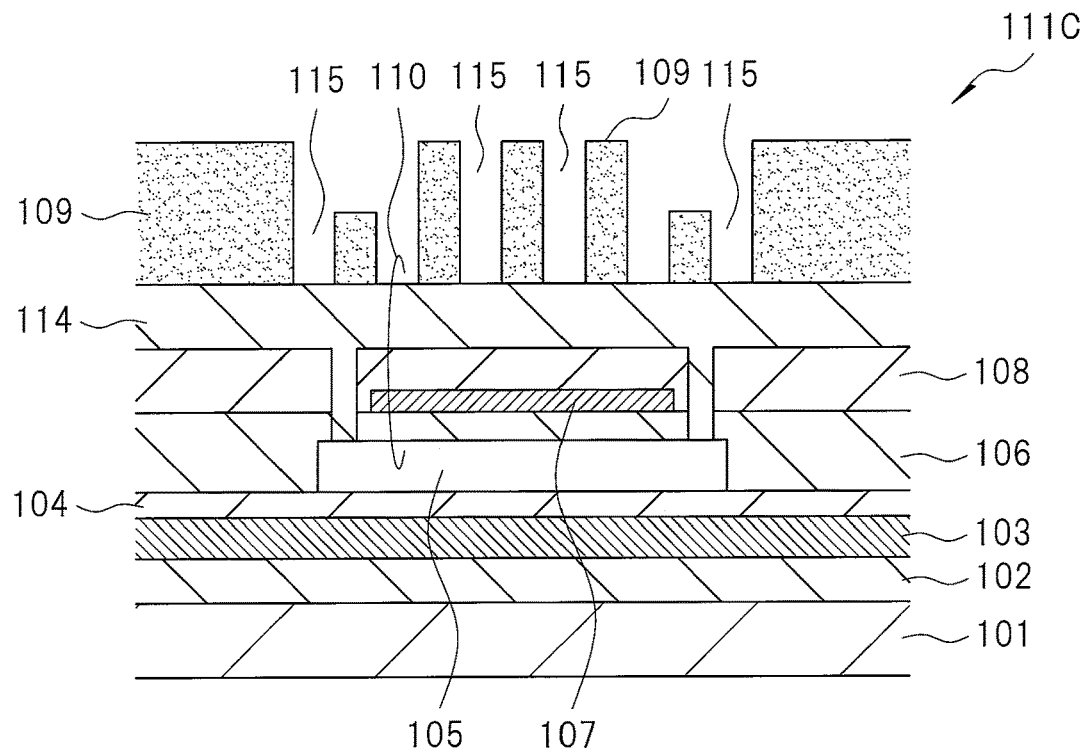
FIG. 10 is a cross-sectional view showing a main part of a capacitive micromachined ultrasonic transducer according to a third embodiment.

FIG. 10 is a cross-sectional view showing a main part of the capacitive micromachined ultrasonic transducer according to a third embodiment. Note that a planar shape of the capacitive micromachined ultrasonic transducer according to the third embodiment is identical to the planar shape of the capacitive micromachined ultrasonic transducer according to the first embodiment (see FIG. 1), and thus, illustrations thereof are omitted as appropriate.

The capacitive micromachined ultrasonic transducer 111C of the third embodiment differs from the capacitive micromachined ultrasonic transducers 111A and 111B of the first and second embodiments in that the thickness of the protective film 109 is not constant. Namely, in the example shown in FIG. 10, the thickness of the protective film 109 above the peripheral portion of the vibration film 110 is relatively thin, whereas the thickness of the protective film 109 above the center portion of the vibration film 110 is relatively thick.

Here, effects of the third embodiment will be described. As described in the second embodiment, the occurrence probability of destruction of the vibration film 110 during the mounting step is higher at the center portion of the vibration film 110 than at the peripheral portion of the vibration film 110. Thus, even if the thickness of the protective film 109 above the peripheral portion of the vibration film 110 is relatively thin, it is considered that there is little influence on destruction of the vibration film 110. On the other hand, from the viewpoint of suppressing a decrease in sensitivity of the vibration film 110, it is preferable that the mass of the protective film 109 is reduced. Namely, the thickness of the protective film 109 above the peripheral portion of the vibration film 110 is configured to be relatively thin, so that a decrease in both yield and sensitivity can be suppressed.

Further, from the viewpoint of creep deformation, the protective film 109 above the peripheral portion of the vibration film 110 has a greater influence on creep deformation than the protective film 109 above the center portion of the vibration film 110 as described in the second embodiment. For this reason, the thickness of the protective film 109 above the peripheral portion of the vibration film 110 is configured to be relatively thin, so that influence on creep deformation can be reduced. In this manner, from the viewpoint of creep deformation, it is preferable that the thickness of the protective film 109 is thinner at the portion above the peripheral portion of the vibration film 110 than at the portion above the center portion of the vibration film 110.

Figure 11:
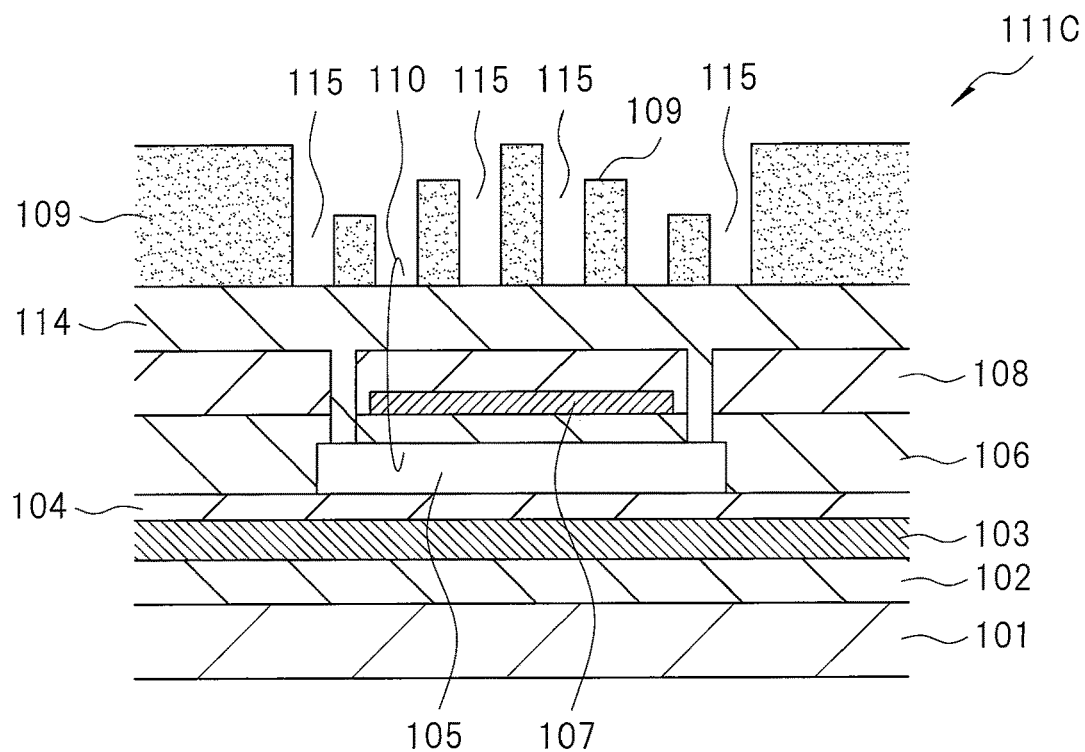
FIG. 11 is a cross-sectional view showing a main part of a modification of the capacitive micromachined ultrasonic transducer according to the third embodiment.

In the above-described example, the protective film 109 has two separate thicknesses between the portion above the peripheral portion of the vibration film 110 and the portion above the center portion of the vibration film 110. However, the thickness of the protective film 109 may be configured so as to gradually decrease from the portion above the center portion of the vibration film 110 toward the portion above the peripheral portion of the vibration film 110 as shown in, for example, FIG. 11.

To summarize, the thickness of the protective film 109 is configured to be thin at the portion above the peripheral portion of the vibration film 110 and be thick at the portion above the center portion of the vibration film 110, so that a decrease in sensitivity of the vibration film 110 and an occurrence of creep deformation can be suppressed without causing a decrease in the manufacturing yield of the capacitive micromachined ultrasonic transducer 111C.

Fourth Embodiment

Figure 12:
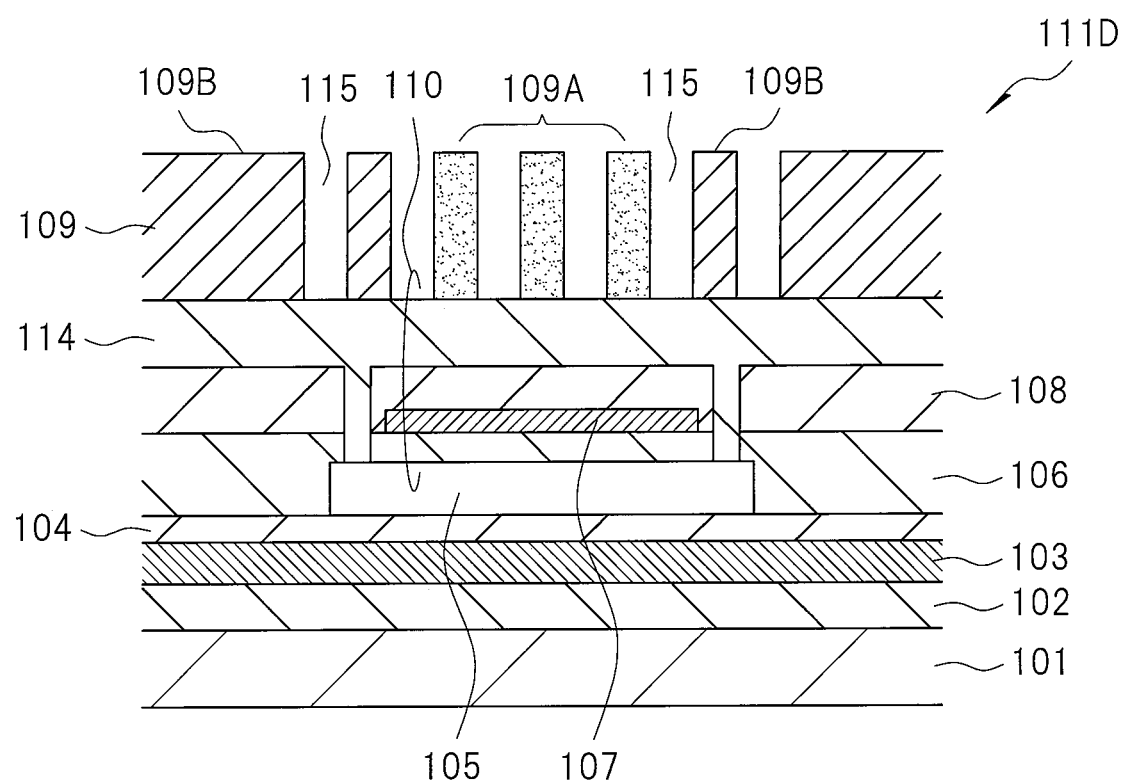
FIG. 12 is a cross-sectional view showing a main part of a capacitive micromachined ultrasonic transducer according to a fourth embodiment.

FIG. 12 is a cross-sectional view showing a main part of the capacitive micromachined ultrasonic transducer according to a fourth embodiment. Note that a planar shape of the capacitive micromachined ultrasonic transducer according to the fourth embodiment is identical to the planar shape of the capacitive micromachined ultrasonic transducer according to the first embodiment (see FIG. 1), and thus, illustrations thereof are omitted as appropriate.

The capacitive micromachined ultrasonic transducer 111D of the fourth embodiment differs from the capacitive micromachined ultrasonic transducers 111A, 111B and 111C of the first, second and third embodiments in that the material of the protective film 109 differs between the portion above the peripheral portion of the vibration film 110 and the portion above the center portion of the vibration film 110. Namely, in the example shown in FIG. 12, the protective film 109B above the peripheral portion of the vibration film 110 is made of a material having a lower Young's modulus than a material of the protective film 109A above the center portion of the vibration film 110.

Here, effects of the fourth embodiment will be described. As described in the second embodiment, the occurrence probability of destruction of the vibration film 110 during the mounting step is higher at the center portion of the vibration film 110 than at the peripheral portion of the vibration film 110. Thus, even if the Young's modulus of the protective film 109B above the peripheral portion of the vibration film 110 is relatively low, it is considered that there is little influence on destruction of the vibration film 110. On the other hand, from the viewpoint of suppressing a decrease in sensitivity of the vibration film 110, it is preferable that stiffness (=product of Young's modulus and a second moment of cross-sectional area) of the protective film 109 is reduced. Namely, the protective film 109B above the peripheral portion of the vibration film 110 is made of a material having a relatively low Young's modulus, so that a decrease in both yield and sensitivity can be suppressed.

Further, from the viewpoint of creep deformation, the protective film 109 above the peripheral portion of the vibration film 110 has a greater influence on creep deformation than the protective film 109 above the center portion of the vibration film 110 as described in the second embodiment. For this reason, the protective film 109B above the peripheral portion of the vibration film 110 is made of a material having a low Young's modulus, so that creep deformation can be suppressed by reducing stress (=product of Young's modulus and strain) applied to the protective film 109B. In this manner, from the viewpoint of creep deformation, it is preferable that the Young's modulus of the protective film 109B above the peripheral portion of the vibration film 110 is lower than the Young's modulus of the protective film 109A above the center portion of the vibration film 110.

In the above-described example, two types of protective films 109A and 109B having different Young's moduli are utilized. However, two or more types of protective films having different Young's moduli may be utilized such that the Young's moduli of the protective films are gradually reduced from the portion above the center portion of the vibration film 110 toward the portion above the peripheral portion of the vibration film 110.

Fifth Embodiment

Figure 13:
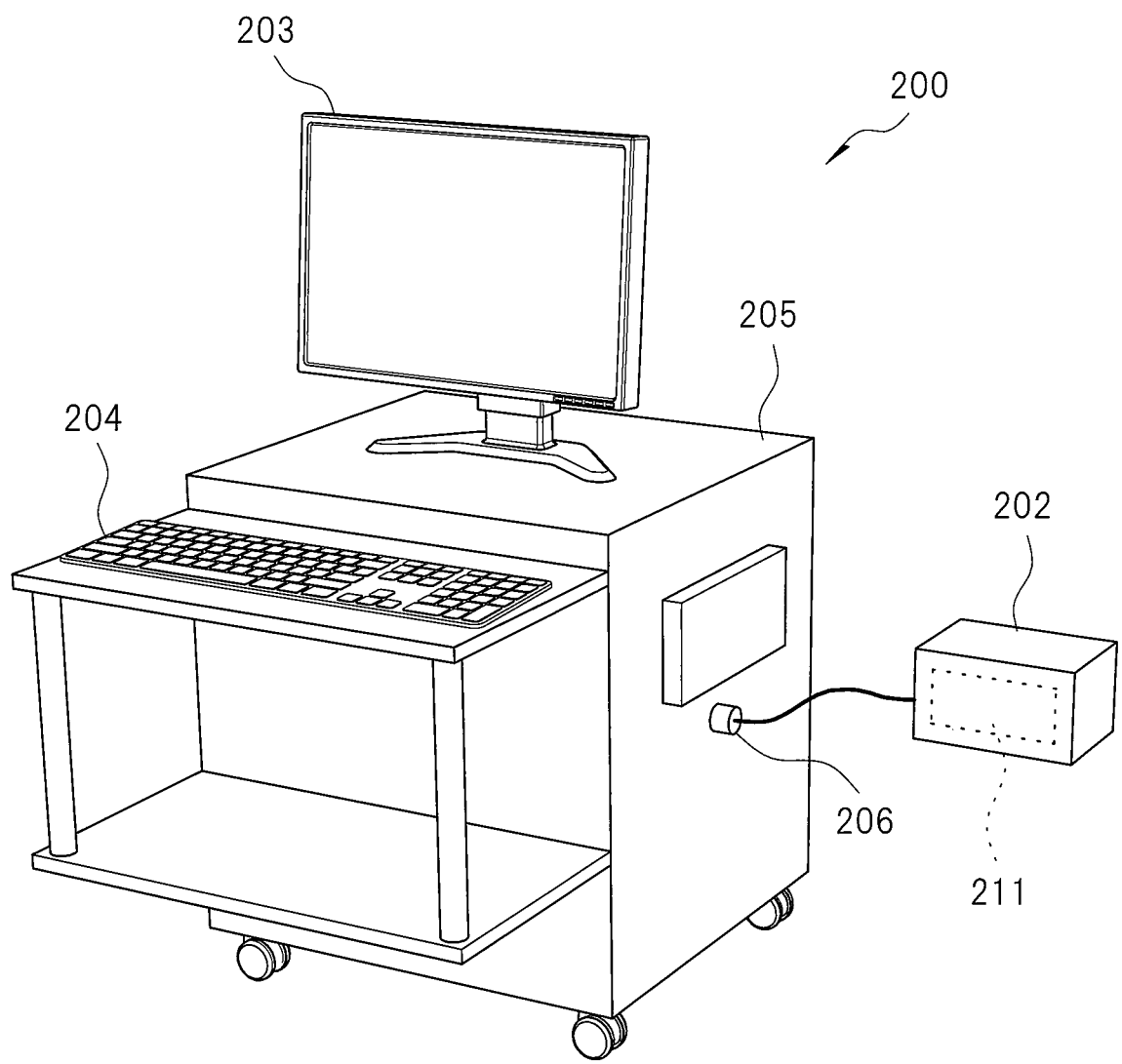
FIG. 13 is a perspective view showing an ultrasonic imaging apparatus according to a fifth embodiment.

FIG. 13 is a perspective view showing an ultrasonic imaging apparatus according to a fifth embodiment. The ultrasonic imaging apparatus 200 of the fifth embodiment has an ultrasonic probe 202, a display 203, an operation unit 204, a signal processor 205 and an ultrasonic transmission circuit 206.

The ultrasonic probe 202 is a unit that is brought in contact with a subject and transmits and receives ultrasonic waves to and from the subject. An ultrasonic wave is transmitted from the ultrasonic probe 202 to the subject, and a reflected echo signal from the subject is received by the ultrasonic probe 202. The ultrasonic probe 202 has a built-in capacitive micromachined ultrasonic transducer 211 electrically connected to the ultrasonic transmission circuit 206.

The signal processor 205 is a unit that forms an image (such as a tomographic image or a blood flow image) based on the reflected echo signal. The display 203 is a unit that displays the image. The operation unit 204 is an instruction unit for the ultrasonic imaging apparatus 200 and is constituted by input units such as a keyboard, a trackball, a mouse and the like.

The ultrasonic imaging apparatus 200 of the fifth embodiment is characterized in that any of the capacitive micromachined ultrasonic transducers 111A, 111B, 111C and 111D of the first to fourth embodiments is utilized as the capacitive micromachined ultrasonic transducer 211 of the ultrasonic probe 202, and as a result, an effect in which a highly sensitive ultrasonic imaging apparatus 200 is provided at a low cost can be obtained.

In the foregoing, the invention made by the present inventors has been concretely described based on the embodiments. However, the present invention is not limited to the foregoing embodiments, and various modifications and alterations can be made within the scope of the present invention.

For example, the configuration of each of the capacitive micromachined ultrasonic transducers 111A, 111B, 111C and 111D of the first to fourth embodiments can be combined with each other as appropriate.

LIST OF REFERENCE SIGNS

101: silicon substrate
102: insulating film
103: lower electrode
104: insulating film
105: cavity
106: insulating film
107: upper electrode
108: insulating film
109, 109A, 109B: protective film
110: vibration film
111A, 111B, 111C, 111D: capacitive micromachined ultrasonic transducer
112, 113: foreign matter
114: insulating film
115: gap
118: metal film
119: cavity-forming hole
200: ultrasonic imaging apparatus
202: ultrasonic probe
203: display
204: operation unit
205: signal processor
206: ultrasonic transmission circuit
211: capacitive micromachined ultrasonic transducer

The invention claimed is:

1. A capacitive micromachined ultrasonic transducer comprising:
    a substrate;
    a lower electrode formed on the substrate;
    a cavity formed in a portion of a first insulating film formed over the lower electrode;
    an upper electrode formed on the first insulating film;
    a second insulating film formed over the upper electrode;
    a protective film formed over the second insulating film; and
    a vibration film constituted by the first insulating film, upper electrode and second insulating film above the cavity,
    wherein the protective film above the vibration film is divided into a plurality of patterns arranged with a gap having a predetermined spacing formed therebetween, and
    wherein a Young's modulus of the protective film above a peripheral portion of the vibration film is lower than a Young's modulus of the protective film above a center portion of the vibration film.

2. The capacitive micromachined ultrasonic transducer according to claim 1,
    wherein a pattern density of the protective film above a peripheral portion of the vibration film is lower than a pattern density of the protective film above a center portion of the vibration film.

3. The capacitive micromachined ultrasonic transducer according to claim 1,
    wherein a film thickness of the protective film above a peripheral portion of the vibration film is thinner than a film thickness of the protective film above a center portion of the vibration film.

4. An ultrasonic imaging apparatus comprising an ultrasonic probe that includes the capacitive micromachined ultrasonic transducer according to claim 1.

5. The capacitive micromachined ultrasonic transducer according to claim 2,
    wherein a planar size of the protective film above the peripheral portion of the vibration film is smaller than a planar size of the protective film above the center portion of the vibration film.

6. The capacitive micromachined ultrasonic transducer according to claim 2,
    wherein the spacing of the gap in the protective film above the peripheral portion of the vibration film is larger than the spacing of the gap in the protective film above the center portion of the vibration film.

* * * * *